United States Patent [19]

Stark

[11] Patent Number: 5,379,238

[45] Date of Patent: Jan. 3, 1995

[54] SIGNAL PROCESSING METHOD AND APPARATUS

[76] Inventor: Edward W. Stark, 160 W. End Ave., Suite 3M, New York, N.Y. 10023

[21] Appl. No.: 923,029

[22] Filed: Jul. 30, 1992

Related U.S. Application Data

[63] Continuation of Ser. No. 815,640, Dec. 30, 1991, abandoned, which is a continuation of Ser. No. 319,450, Mar. 3, 1989, abandoned.

[51] Int. Cl.$^6$ .................. A61B 5/00; G06G 7/48; G06F 15/42
[52] U.S. Cl. .................. 364/578; 128/633; 324/322; 356/39; 364/413.07; 364/498; 364/574
[58] Field of Search .............. 364/573, 574, 498, 578, 364/413.07, 413.08, 413.09; 324/312, 322; 356/39, 40; 128/633

[56] References Cited

U.S. PATENT DOCUMENTS

| | | | |
|---|---|---|---|
| 4,014,321 | 3/1977 | March | 356/39 X |
| 4,017,192 | 4/1977 | Rosenthal | 356/39 X |
| 4,167,331 | 9/1979 | Nielsen | 356/39 |
| 4,412,341 | 10/1983 | Gersho et al. | 364/574 X |
| 4,791,577 | 12/1988 | Winter | 364/574 X |
| 4,837,720 | 6/1989 | Rambaut | 364/574 |
| 4,863,265 | 9/1989 | Flower et al. | 128/633 X |

*Primary Examiner*—Emanuel T. Voeltz
*Assistant Examiner*—Edward J. Pipala
*Attorney, Agent, or Firm*—McAulay Fisher Nissen Goldberg & Kiel

[57] ABSTRACT

A method and apparatus for the determination of spectral samples is disclosed wherein spectral measurements are taken, normalization of the spectral measurements takes place, and a bilinear modeling is performed to extract spectral data. Once this data is derived, the interference quantitization levels are determined using multiple linear regression analysis, and are then removed from the sample readings in order to determine a more precise level of analyte spectra, such as analyte levels of glucose in serum or whole blood.

2 Claims, 3 Drawing Sheets

SIGNAL PROCESSING METHOD AND APPARATUS

This application is a continuation of application Ser. No. 815,640 filed Dec. 30, 1991 abandoned, which is a continuation of Ser. No. 319,450 filed Mar. 3, 1989, abandoned.

FIELD OF THE INVENTION

The present invention relates generally to processing of data signals to reduce undesired variations or noise present in the data. Specifically, the present invention relates to an instrument or method for processing of data signals to reduce undesired variations or noise present in data. Most specifically, the present invention relates to an instrument, method or process to provide measurements of analytes reduced from data by removing undesired variations and noise present in that data.

BACKGROUND OF THE INVENTION

Sensors are used to measure physical phenomena and to convert the measured values into data values. The magnitudes of these data values are presented as data signals. The measurement process itself will generally introduce errors and unwanted variations in the data values. In addition, additional errors and noise may be introduced in the conversion and transmission of data signals. In most cases, it is desired to extract from the data signals the data values associated with one or more "analytes", that is the magnitude of a specific physical phenomena. When a sequence of measurements is made, an additional dimension is added to the data signal structure, that is, an additional data point index is created relating the data values to the measurement sequence. For example, a single measurement, such as temperature, made at a sequence of times or on a series of specimens yields a stream of data values with one dimensional point index. Two dimensional data point index structures result when each measurement in a sequence produces a "spectrum" consisting of multiple interrelated data values, such as an optical spectrum or a chromatogram.

Noise and variation in such data structures are often assumed to be random and unrelated among the data values. With such random data, the most direct approach to reducing variation and noise is in a weighted averaging of such data values. This is typically done by averaging the spectral data values of several spectra from the sequence of spectra, for instance, in combining measurements having the same spectral data point index, or "wavelength". Another typical approach is the weighted averaging the data values of several adjacent data points within each spectrum. In many instances, both types of averaging are often combined, to produce more precise measurements of data, and to further reduce effects of any variations or random noise in the data. Averaging assumes that no interrelationship exist among the data values. If the data values are interrelated, there have also been developed a large number of multivariate methods of processing data signals to reduce noise and unwanted variations. In general, these methods are based on each data value containing several parts or components each related to a different physical phenomenon and, therefore, on each spectrum consisting of several "spectral components" characteristic of the associated physical phenomenon. Each spectral component consists of a set of data values and their associated data point indices. A spectral component may be represented by a data signal. These techniques have included, for example, such methods as least mean square methods of curve fitting various spectra. With this technique, each spectrum from the data set is approximated as a linear combination of the spectra of known constituents or components within the data. These approximations satisfy a least mean square criterion. The appropriate coefficients of these linear combinations are then linearly related with, typically, analyte concentrations in the specimens.

Curve fitting methods have been extended in various respects. First, multilinear correlation of several of the derived curve-fit coefficients with analyte values is accomplished to reduce the errors. Second, measured spectra from specimens of known compositions, rather than pure constituent spectra, are used as components. Errors are reduced using these techniques such that they become comparable to those obtained by multilinear regression using unmodified or derivative type data at selected wavelengths. Yet, such methods assume a previous knowledge of the reference spectra. As well, these methods are not applicable to situations where the interfering spectra have variable characteristics.

Other methods have included techniques such as spectral subtraction, where interferences are reduced by subtracting previously known or estimated reference spectra based on prior information about such spectra. For instance, in cases in which optical absorption spectra are used, it is known that such spectra will never be negative. Accordingly, once an absorption difference spectrum is estimated to be approximately at one or more data points, it is no longer desirable to subtract a greater interference magnitude from this spectrum. At that point, the combined interference spectrum is set, and the estimate of the analyte spectrum is obtained.

Other higher level techniques have included such methods as latent variable analysis or bilinear modeling. In these methods, underlying sets of data values, or latent spectra, are extracted statistically from a data set. These method include, among others, factor analyses, principal component analysis (PCA) and partial least square (PLS) methods. In these systems, a priori knowledge of the previously derived latent reference spectra are used as the spectral components throughout later analyses. In other words, once a latent reference spectral estimate is made, these higher level techniques inflexibly set the latent reference spectra.

All these previous techniques become inaccurate if the measuring instrument or conditions change significantly. In addition, these previous techniques are incapable of differentiating between the spectral component due to the mimicked analyte spectral component within the interference spectra. For instance, where interference spectral components of the data signal bear a correlation to the analyte spectral component, in many of the previous methods it is possible for the interference spectral component of the data signal to be confused with the analyte spectra, producing serious errors in the approximation techniques. Various methods have been proposed to correct these errors, but only after they have occurred.

SUMMARY OF THE INVENTION

Accordingly, it is an object of the present invention to determine the spectral components which interfere with measured data as these components are actually present in the data signals, rather than using a priori knowledge of these interfering components to fit the measured data for interference estimates and reduction.

It is a second object of the present invention to improve estimates of the interference spectra by removing intercorrelation between analyte spectral data values and interference spectral data values in the data signals.

It is a third object of the present invention to improve estimates of the degree of interference, independent of analyte and interference concentrations in the data signals, by removing intercorrelations between the analyte spectral data values and interference spectral data values within the data signals spectra.

It is yet another object of the present invention to correct interferences within the data signals by a more accurate determination of the character and magnitude of these interferences.

It is an additional object of the present invention to subtract interference spectral component data values from the measured data values based on the improved estimates of the character and magnitude of the inference signal components and eliminate these interferences substantially completely from the measured data to improve the ultimate determination of analytes within the originally measured data.

Finally, it is an object of the present invention to incorporate the more accurate measurements of desired data values through subtraction of these interference spectral component values in a method and apparatus for accurate measurements of analytes. It is most desireable to incorporate these methods and apparatus in an apparatus to measure analyte levels, including such methods as taking near infrared measurements of analyte levels in blood, especially the measurement of glucose levels in whole blood or blood products.

These and other objects of the present invention are accomplished in a method wherein spectral characteristics interferences are not considered a priori information, but are derived from data signals as they are being measured, using bilinear modeling, on a of data values set consisting of one or more replicate groups of spectral signals. That is groups of spectral signals for which the analyte magnitude is substantially constant within each replicate group of spectral measurements. The replicate group average spectral signal of each replicate group is subtracted from each spectral signal within the group. Within each replicate group, the analyte spectral signal is constant, and will be contained in the average spectral signal which is subtracted. Once the appropriate replicate group average spectrum is subtracted data values from , multiple replicate groups of spectral signals may be combined into a larger data set for the bilinear modeling to determine latent variable interference spectral data values. Thus, the components of the bilinear model are derived from the set of modified spectral data values, after removal of the replicate group average spectral data values from each set of spectral data values in each replicate group of spectral data values. These will spectral component data values will be used to explain variance in the measured data. Even if the analyte concentration changes between the replicate groups, of measurements the analyte variance is zero, because the analyte signal has been removed by subtracting the replicate group average spectral signal. Thus, the bilinear modeled component data valued represent the spectra of variable interferences and do not include significant analyte information.

Despite the removal of the analyte signal from the data signal prior to bilinear modeling, the resultant latent variable interference spectral data values will usually be correlated to some degree to the analyte spectral shape. This correlation could cause errors in estimating the magnitude of each interference. Therefore, the spectrum of each of the interferences, whether known a priori or derived, is projected on the analyte spectral data values to find the portion of each interference which is unique, i.e., orthogonal to the analyte spectrum. Each interference spectrum will be equal to the sum of its unique portion and a certain amount matching or mimicking the analyte spectrum in spectral characteristics. Projection of each measured spectrum on the unique portions of the interferences (for instance by regression analysis) provides coefficients to represent an estimate of the amount of each interference present in each measured spectrum.

Each set of spectral data values for the unique interference portion is orthogonal to the set of analyte spectral data values. Thus, these estimates of interference magnitude are not biased by the analyte concentration. For each interference, the coefficients of the unique portion can be applied to the original spectral data values of the interference to determine the amount of that interference spectral signal to subtract from the measured spectral data in order to eliminate that portion of the interference. To insure that the measured spectral data are replicates with respect to the analyte, the present invention may include a step of normalizing the measured spectral intensity so that the analytes' spectral signal is kept constant for constant analyte concentration.

These and other objects of the present invention are accomplished in connection with the following discussion the drawings as well as a detailed description of the inventions in which:

DETAILED DESCRIPTION OF THE DRAWINGS

DETAILED DESCRIPTION OF THE PRESENT INVENTION

The present invention has general applicability in the field of signal and data processing, wherever a sequence of "spectra" or data structures consisting of multiple interrelated data values, are obtained and the desired variability in the data can be described as "spectral" patterns. One dimension of the two dimensional data structure can be considered a "sequence", with the other dimension representing the data point indices of the spectra. In these cases, which are the rule rather than the exception, this method is effective in reducing unwanted variability and noise.

As an example, optical spectroscopy, for instance, in the determination of analyte levels in blood using near infrared techniques, often exhibits interferences which change from measurement to measurement due to unavoidable changes in the measurement geometry, the composition of matrix surrounding the analyte, or physical factors such as bulk density, scattering, temperature, bubbles, cavitation, other flow effects, and similar phenomena. Such problems are common in regular transmission, diffuse reflection, diffuse transmission and interaction measurements. The precision of on-line process control measurement of clear liquids is usually limited by variable compositional or physical interferences rather than truly random noise.

Figure 1:
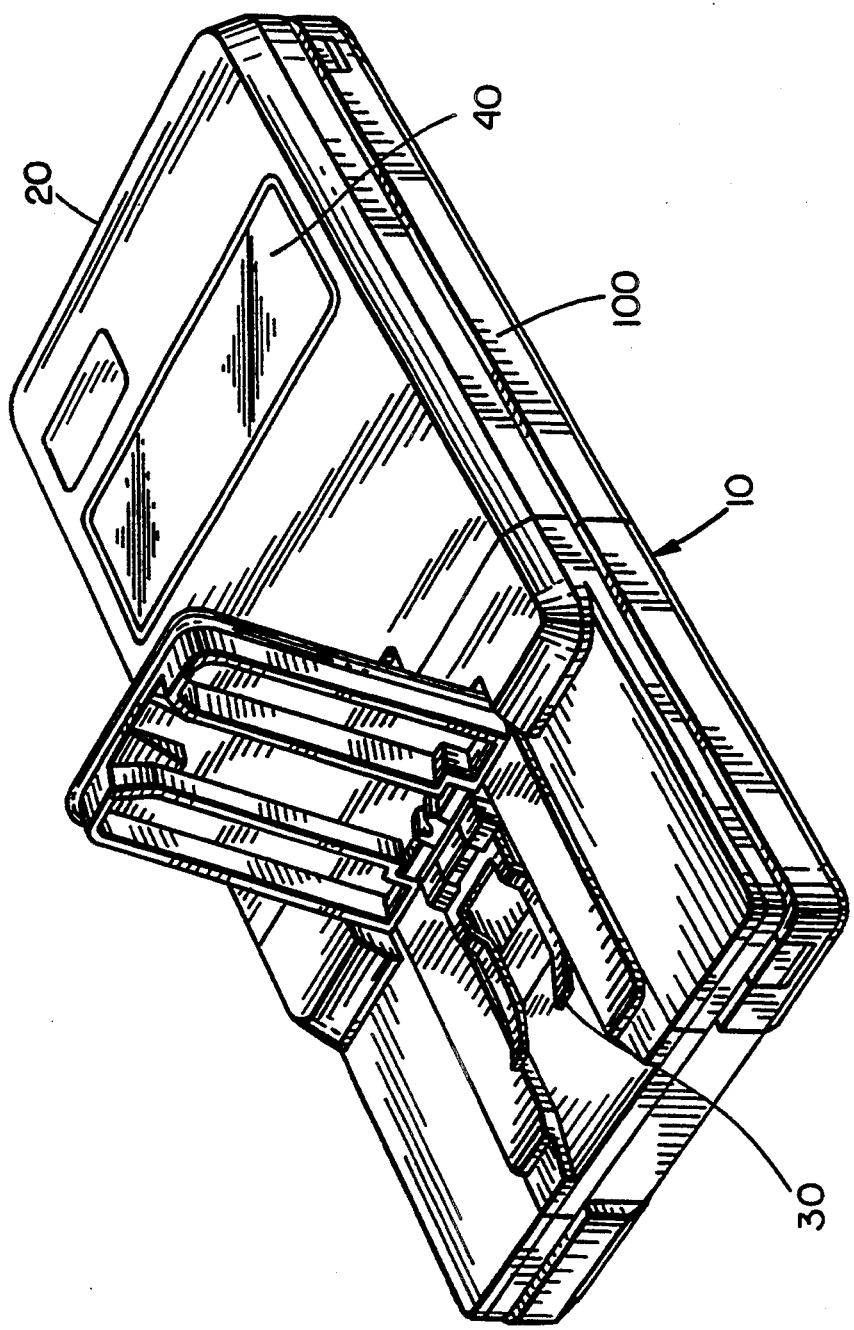
FIG. 1 is a perspective view of a spectrophotometric sensor system for use in performance of the methods and apparatus of the present invention.
Figure 2:
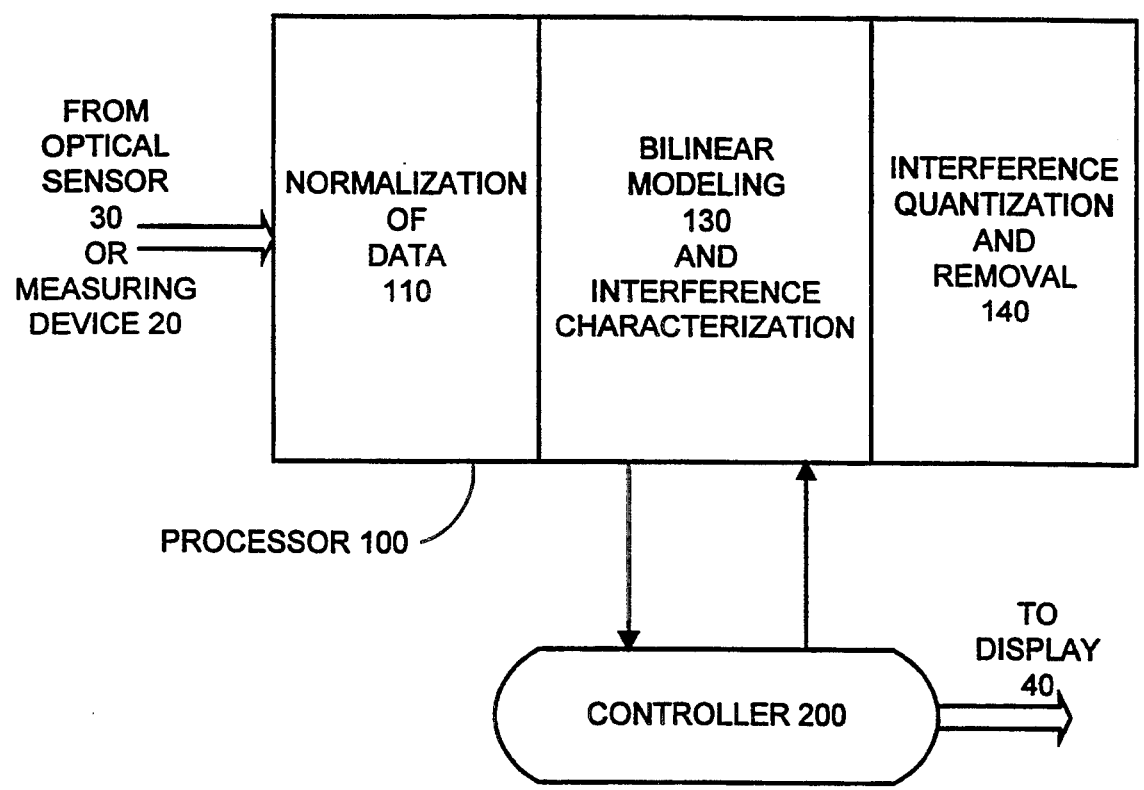
FIG. 2 is a general block diagram of the apparatuses used as components in conjunction with the present invention as shown in FIG. 1.

As can be seen from FIG. 1, for instance, a spectrophotometric sensor system 10 as used in the present invention is described. This system can be used, for instance, in the determination of analyte levels in blood or, for instance, in the display of glucose levels in blood. This sensor system 10 comprises a measuring device 20 with an optical sensor 30 which will data signals corresponding to give optical readings of spectral data values, for instance, spectrophotometric measurements of specimens or materials such as blood. From this measuring device 20 the processor 100 used in conjunction with the method of the present invention is attached. This can be seen in FIG. 2. From the processing unit 100, a controller/analyzer 200 is attached, which allows the processed data to be analyzed and the processing unit 100 is to be controlled based on the data analysis results. The data, after analysis, is sent to display 40.

The processor 100 of the present system follows a five-step approach: a) The processor 100 takes the specimen-derived spectral data from the measuring sensor device 20 and normalizes the data. b) After this optional normalization, the processor extracts the data values for the variable interference spectral components from the data signals. c) The data values of these components are then separated by regression with the analyte spectral data values to remove the portion of the interference signal which mimicks the analyte signal. d) The magnitudes of the interferences are determined by multiple regression of the data values of each measured spectrum on the data values of analyte-orthogonal interferences. Finally, e) the originally extracted interferences are scaled by these magnitudes and subtracted from the original normalized data values in order to finally provide a corrected spectral for use in controller/analyzer 200 to determine the analyte levels. It is these which are ultimately displayed in the display unit 40 of the system 10. If desired, steps c) through e) can be repeated for additional analytes.

The present application now turns to the five distinct functions taking place in the processing unit 100 of the system. Each of the measured spectra, $S_n$, is sequentially stored in the group storage area 112 of the normalizing portion 110 of the processor 100. From this group storage area 112, each set of the spectral data values $S_n$ from a replicate group is added together and divided by the number of measurements in the group in order to determine the average spectral data values, S at averager 115.

Thus, the spectra can be described as in equation (1) below:

$$S_n = b_{on} + b_{on} + b_{ln}\overline{S} + S'_n \qquad (1)$$

In equation (1), $S'_n$ is described as variations in individual spectra from the average spectrum, $\overline{S}$. The coefficient $b_{on}$ represents an additive offset in the measured spectral data, and the coefficient $b_{ln}$ corresponds to a multiplicative scale factor relating spectrum $S_n$ to the average spectrum.

A normalized or corrected spectral data values; $\hat{S}_n$ are then derived using equation (3) in the adder/divider element 116 of the normalization unit 110:

$$\hat{S}_n = \frac{S_n - b_{on}}{b_{ln}} \qquad (3)$$

From equations (3) and (1), showing $$\hat{S}_n = \overline{S} + \frac{S'_n}{b_{ln}}$$

that all the differences, $S'_n$, from the average have been normalized by the factor $b_{ln}$. In order to further proceed toward the ultimate determination of analyte levels, spectral data values describing the interferences should be extracted, but only on variable components, and not on components to be determined, such as analyte levels. Therefore, the newly derived $\hat{S}_n$ are once again grouped in the group storage unit 132 of the interference characterization section 130 of the processor 100. From this replicate group data an average, $\hat{S}_{avg}$, is taken. Then, each $\hat{S}_n$ has subtracted from it the $\hat{S}_{avg}$ to arrive at a newly derived $\hat{S}'_n$ as in equation (6):

$$\hat{S}'_n = \hat{S}_n - \hat{S}_{avg} \qquad (6)$$

Now each of the newly derived $\hat{S}'_n$ will not contain any contributions from the desired analyte spectral data signals.

As each individual $S'_n$ is derived, it is stored in the combined group storage unit 134 in the interference characterization portion 130. Once a desired number of replicate groups of $\hat{S}'_n$ data are stored, they are used as a set within the components analyzer 136. In using known methods of bilinear modeling such as PCA, the set of spectral data $\hat{S}'_n$ are analyzed and broken into components $P_i$-$P_j$. It is known, however, that each of these components $P_1$-$P_j$ are mutually orthogonal.

Thus, the derived $P_j$ components data are now ready for input into the interference quantization and removal area 140 of processor 100. In most instances, the spectrum of the derived components $P_j$, will have some similarity to the known spectrum of the analyte, for instance, glucose. In these cases, the correlation between the two spectra will not equal zero, and regressing of the spectral data $S_n$ on the interfering components $P_j$ would produce incorrect coefficients influenced by analyte concentration. Thus, the derived components must be modified in order to appropriately orthogonalize these components with respect to the analyte. This is accomplished by removing the entire portion of the interference (component spectrum $P_j$) which mimics the analyte.

Thus, the individual derived component data values, $P_j$, are put into a simple linear regression analyzer 142. Data values of each component $P_j$ are projected on the data values of known analyte reference spectrum, A from reference area 141. After the linear regression is accomplished, coefficient data values quantifying the analyte like portion $c_j$ are derived for each individual component $P_j$.

These coefficient data values $c_j$ are multiplied by the known analyte spectrum A to determine the portion of each component spectral data $P_j$ which mimics the analyte spectral data A. Thus, a modified spectral principal component $Q_j$ can be derived at combiner 143 at for each $P_j$ as in equation (7):

$$Q_j = P_j - c_j A \qquad (7)$$

Importantly, each $Q_j$ will now be orthogonal to the analyte spectrum A. As a check on these operations, coefficient $C_{oj}$ should be derived, where $C_{oj}$ should equal zero.

Now, the previously stored corrected individual spectra $\hat{S}_n$ can be analyzed using the modified components data $Q_j$ in order to determine the magnitude of each component $Q_j$ spectral signal contained in each group corrected individual $\hat{S}_n$. As seen in the interference quantization and removal section 140, a multiple linear regression analysis at analyzer 144 is performed regressing each the data values of $\hat{S}_n$ on the data values of $Q_j$ components to arrive at coefficient data values $m_{jn}$ where each of the $m_{jn}$ conforms to equation (8):

$$\hat{S}_n = m_{on} + \sum_j m_{jn} Q_j + \epsilon \qquad (8)$$

As seen in equation (8), the $m_{0n}$ are described as offsets of the spectral data.

Now data values of the newly derived factors $m_{jn}$ can be combined with the data values of the components $P_j$ at multiplier 145 in order to determine the actual interference component spectra, data values $I_{jn}$, in each specimen, according to equation (9):

$$I_{jn} = m_{jn} P_j \qquad (9)$$

Figure 3:
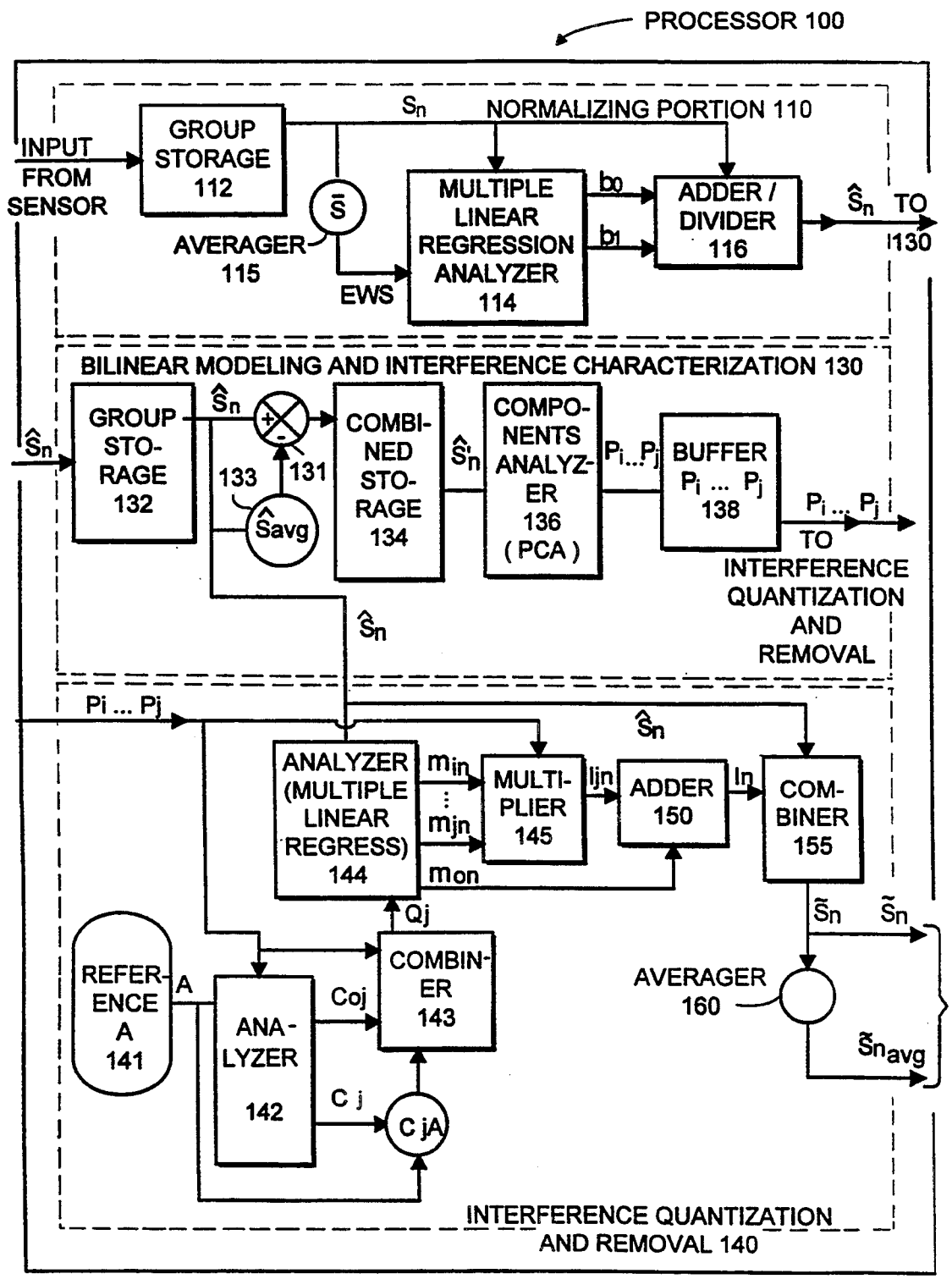
FIG. 3 is a block diagram of the processor unit as used in the present invention.

One remaining step is necessary to determine the entire interference spectral signal contained in the spectral signal of specimen each. Thus, each individual interference component, $I_{jn}$, is placed into a vector adder 150 as seen in FIG. 3. The corresponding data values of each of the interference components is summed. The offset data value m is added on to this factor according to equation (10):

$$I_n = m_{on} + \sum_j I_{jn} \qquad (10)$$

Now, the interference spectral data values derived for each specimen, $I_n$, can be removed from the corrected individual spectra $\hat{S}_n$. At combiner 155, as in equation (11), the sum of the interference components, $I_n$, is subtracted from the corrected individual spectra $\hat{S}_n$ to arrive at the final corrected spectral data $\overline{S}_n$:

$$\overline{S}_n = \hat{S}_n - I_n \qquad (11)$$

Of course, in order to more clearly approximate the $\hat{S}_n$ and reduce residual random errors, an average can be taken at averager 160 in the final step of the interference quantitization and removal process. Thus, the newly arrived average final corrected spectral data $\overline{S}_{navg}$ will most accurately parallel the level of analyte that is present in the specimen.

Optionally, it is possible to use a buffer 138 as seen in the same step in order to prevent changes in analyte levels within a replicate group from causing errors. For instance, in cases where a presumed constant analyte level actually changes, these changes can be monitored by controller/analyzer 200 using the output signal $\overline{S}_n$. If the analyte variation within a replicate group of measurement is larger than a predetermined amount, the inference component data values derived during the present derivation are determined to be inaccurate, and previously stored ones are used.

While the present application has been described in connection with a presently preferred embodiment, it will be recognized that the invention is to be determined from the following claims and their equivalents.

What is claimed is:

1. In a method for determining analyte levels for displaying glucose levels in blood using near infrared techniques including the steps of:

measuring glucose levels of a parameter related to blood using near infra-red optical techniques to provide a set of signals representing spectral data, said spectral data including spectral components resulting from physical properties of an environment in which measurement takes place which components interfere with the measured data; and processing said spectra-representing signals having said interfering spectral components by:

removing the effect of constant analyte contribution by subtracting signals representing average spectra of replicate groups of said spectral data to form signals representing modified spectra representing variable interference information;

determining signals representing component spectra of said modified spectral signals by bilinear model analysis;

determining signals representing the magnitude of each said component spectra contained in each original spectrum and applying these signals representing magnitudes to signals representing component spectra to develop signals representing interference spectra; and removing said signals representing the resulting interference spectra from said signals representing said original spectra for producing corrected spectral signals representing said spectral data of glucose blood levels with said interference components removed.

2. Apparatus for processing signals representing measured spectral data for removing effects of spectral components which interfere with said measured data in determining analyte levels and in displaying glucose levels in blood using near infrared techniques comprising:

means for measuring glucose levels of a parameter related to blood using near infrared optical techniques to provide a set of signals representing spectral data, said spectral data including spectral components resulting from physical properties of an environment in which measurement takes place which components interfere with the measured data;

means for processing said spectra-representing signals having said interfering spectral components including:

a subtractor for removing the effect of constant analyte contribution by subtracting signals representing the average spectra of replicate groups of said spectral data to form signals representing modified spectra representing variable interference information;

a components analyzer for determining representative signals of component spectra of said modified spectra by bilinear model analysis;

an analyzer for determining signals representing the magnitude of each said component spectra contained in each original spectrum and means for applying these magnitude-representing signals to the component spectra to develop signals representing interference spectra; and a combiner for removing said signals representing the resulting interference spectra from said signals representing said original spectra for producing corrected spectral signals representing said spectral data of glucose blood levels with said interference components removed.

* * * * *